US00PP10387P

United States Patent [19]

Zaiger et al.

[11] Patent Number: Plant 10,387

[45] Date of Patent: May 12, 1998

[54] PEACH TREE 'VALLEY SWEET'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 784,490

[22] Filed: Jan. 17, 1997

[51] Int. Cl.[6] ..... A01H 5/00

[52] U.S. Cl. ..... Plt./43.2

[58] Field of Search ..... Plt./43.2

*Primary Examiner*—James R. Feyrer

[57] ABSTRACT

A new and distinct variety of peach tree (*Prunus persica*) which has the following unique combination of desirable features that are outstanding in a new variety:

1. Heavy and regular production of large size fruit.
2. Fruit with very good flavor and eating quality.
3. Relatively uniform fruit size throughout the tree.
4. Fruit with a high degree of attractive red skin color.
5. Fruit that will hold firm on the tree 6–7 days after maturity (shipping ripe).
6. Vigorous and upright growth.

1 Drawing Sheet

ORIGIN OF THE VARIETY

The new variety of peach tree was developed by us in our experimental orchard located near Modesto, Calif., as a fourth generation seedling from a cross between two selected seedlings, field identification numbers 25GA440 and 16RA384. The maternal parent (25GA440) originated from a cross between a Flavortop Nectarine (non-patented) with a seedling selection which originated from a Sun Red Nectarine (non-patented) crossed with Spring Grand Nectarine (U.S. Plant Pat. No. 2,767). The pollen parent (16RA384) originated from a cross between a Redwing Peach (U.S. Plant Pat. No. 621) with a very firm, high colored nectarine of unknown parentage. A large group of these open pollinated seedlings were grown and maintained under close observation by us, during which time one such seedling, which is of the present variety, exhibited especially desirable fruit characteristics and was selected for asexual reproduction and commercialization.

ASEXUAL REPRODUCTION OF THE VARIETY

Asexual reproduction of the new and distinct variety of peach tree was by budding, as performed by us in our experimental orchard located near Modesto, Calif., and shows that characteristics of the tree and its fruit run true to the original tree and are established and transmitted through succeeding asexual propagations.

SUMMARY OF THE VARIETY

The present new variety of peach tree is of large size, vigorous, upright growth, and is a regular and productive bearer of large, firm, yellow flesh, freestone fruit with a high degree of attractive red skin color. The fruit is further characterized by being relatively uniform in size throughout the tree, holding firm on the tree 6–7 days after maturity (shipping ripe), and having good storage and shipping quality; in comparison to O'Henry Peach (U.S. Plant Pat. No. 2964) the tree of the new variety produces fruit more uniform in size throughout the tree, has a higher degree of attractive red skin color, with sweet subacid flavor, and is approximately 10 days earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and a stone remaining in place. The photographic illustration was taken shortly after being picked (shipping ripe) and the colors are as nearly true as reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Productivity.*—Productive.
- *Bearer.*—Regular.
- *Density.*—Medium dense.
- *Shape.*—Usually pruned to vase shape.

Trunk:
- *Size.*—Medium to large.
- *Texture.*—Medium shaggy.
- *Color.*—Brown to tobacco brown (5-E-5) to (5-F-6).

Branches:
- *Size.*—Medium to large.
- *Texture.*—Smooth to medium rough, varies with age of growth.
- *Lenticels.*—Medium number. Medium size.
- *Color.*—Light brown to brown, varies with maturity.

Leaves:
- *Size.*—Large. Average length 6". Average width 1½".
- *Form.*—Lanceolate, pointed.
- *Margin.*—Crenate.
- *Thickness.*—Medium.
- *Surface.*—Smooth.
- *Petiole.*—Medium length. Medium thickness.
- *Glands.*—Number varies from 1 to 4. Average number 2. Reniform. Medium size. Located on base of leaf blade and upper portion of petiole.
- *Color.*—Upper surface — green to dark green (28-E-7) to (28-F-7). Lower surface — dull green to green (28-D-8) to (28-E-8).

Flower buds:
*Size.*—Medium to large.
*Length.*—Medium.
*Form.*—Plump.
*Pubescence.*—Pubescent.
Flowers:
*Size.*—Large, showy.
*Pollen.*—Present, self-fertile.
*Blooming Period.*—Date of first bloom: Mar. 2, 1996. Date of full bloom: Mar. 8, 1996. Varies slightly with climatic conditions.
*Color.*—Pink.
Fruit:
*Maturity when described.*—Firm ripe.
*Date of first picking.*—Jul. 8, 1996.
*Date of last picking.*—Jul. 13, 1996. Varies slightly with climatic conditions.
*Size.*—Large. Average diameter axially 2¾" to 2⅞". Average transversely in suture plane 2⅞" to 3".
*Form.*—Nearly globose. Slightly flattened at stem end.
*Suture.*—Shallow, extends from base to apex.
*Ventral surface.*—Nearly round, varies from rounded to slightly lipped.
*Apex.*—Usually rounded, varies from rounded to slight apical point.
*Base.*—Retuse.
*Cavity.*—Rounded, slightly elongated in suture plane. Average depth ½". Average width 1".
Flesh:
*Ripens.*—Evenly.
*Texture.*—Firm.
*Fibers.*—Few, small, tender.
*Aroma.*—Moderate.
*Amygdalin.*—Undetected.
*Eating quality.*—Very good.
*Flavor.*—Very good, sweet, subacid.
*Color.*—Varies from light yellow to yellow (3-A-5) to (3-A-7). Pit cavity — red to wine red (11-D-6) to (11-D-8). Slight bleeding from pit cavity into flesh.
Skin:
*Thickness.*—Medium.
*Texture.*—Medium, tenacious to flesh.
*Down.*—Moderate Medium in length.
*Tendency to crack.*—None.
*Color.*—Light yellow to yellow ground color (3-A-4) to (3-A-6). Overspread with red to wine red (11-D-6) to (11-D-8).
Stone:
*Type.*—Freestone.
*Size.*—Medium to large. Average length 1¼". Average breadth 1". Average thickness ⅝".
*Form.*—Usually obovoid. Varies from obovoid to ovoid.
*Base.*—Usually rounded, varies from rounded to straight.
*Apex.*—Cuspidate.
*Surface.*—Irregularly furrowed toward apex, pitted toward base, pits vary from round to elongated.
*Sides.*—Equal to unequal.
*Tendency to spilt.*—None.
*Color.*—Reddish brown to dark brown (8-E-8) to (8-F-8).
Use: Dessert.
*Market.*—Local and long distance.
Keeping quality: Good.
Shipping quality: Good.

The present new and distinct variety of peach tree, its flowers, foliage and fruit herein described may vary in slight detail due to cultural practices, soil types and climatic conditions and under which the variety may be grown. The present description is of the variety grown under the ecological conditions prevailing near Modesto, Calif.

We claim:

1. A new and distinct variety of peach tree, substantially as illustrated and described, characterized by its large size, vigorous and upright growth, is a regular and productive bearer of large, firm, yellow flesh freestone fruit with sweet, subacid flavor; the fruit is further characterized by being relatively uniform in size throughout the tree, holding firm on the tree 6–7 days after maturity (shipping ripe) and, in comparison to O'Henry Peach (U.S. Plant Pat. No. 2,964), the fruit has a higher degree of attractive red skin color and is approximately 10 days earlier in maturity.

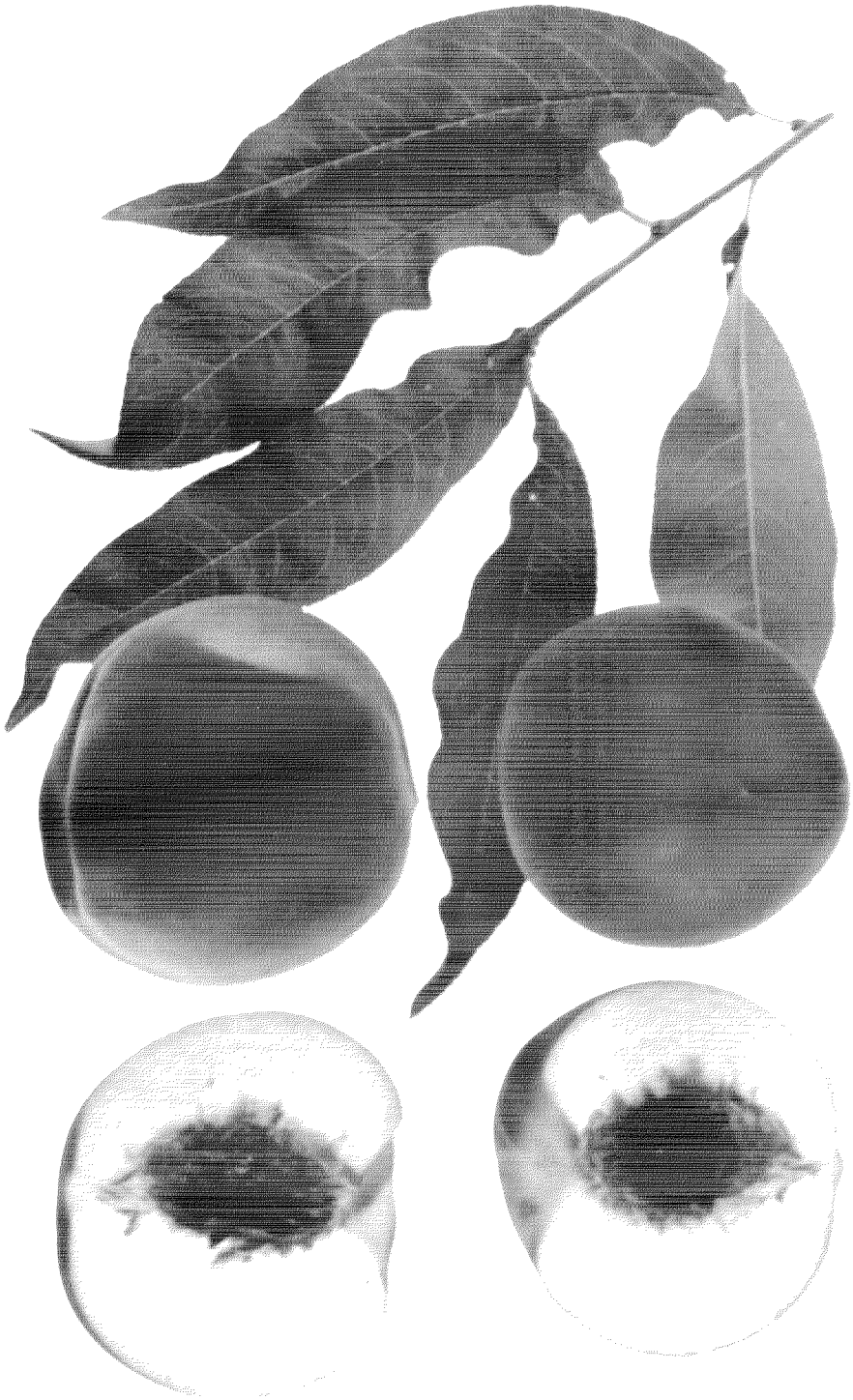

* * * * *